(12) United States Patent
Singh et al.

(10) Patent No.: US 9,779,843 B2
(45) Date of Patent: Oct. 3, 2017

(54) RADIOACTIVE MATERIAL STORAGE CANISTER

(71) Applicant: Holtec International, Inc., Marlton, NJ (US)

(72) Inventors: Krishna P. Singh, Hobe Sound, FL (US); John D. Griffiths, Deptford, NJ (US); Joseph Albert Meckley, Marlton, NJ (US)

(73) Assignee: HOLTEC INTERNATIONAL, INC.

( * ) Notice: Subject to any disclaimer, the term of this patent is extended or adjusted under 35 U.S.C. 154(b) by 200 days.

(21) Appl. No.: 14/655,860

(22) PCT Filed: Dec. 26, 2013

(86) PCT No.: PCT/US2013/077852
§ 371 (c)(1),
(2) Date: Jun. 26, 2015

(87) PCT Pub. No.: WO2014/105977
PCT Pub. Date: Jul. 3, 2014

(65) Prior Publication Data
US 2015/0340112 A1 Nov. 26, 2015

Related U.S. Application Data

(60) Provisional application No. 61/746,094, filed on Dec. 26, 2012.

(51) Int. Cl.
| | | |
|---|---|---|
| G21F 5/00 | (2006.01) |
| G21F 5/008 | (2006.01) |
| B65D 8/00 | (2006.01) |
| B65D 6/32 | (2006.01) |
| B23K 5/08 | (2006.01) |
| B23K 9/028 | (2006.01) |
| B23K 9/18 | (2006.01) |
| B23K 10/02 | (2006.01) |
| B23K 11/093 | (2006.01) |
| B23K 23/00 | (2006.01) |
| B23K 25/00 | (2006.01) |
| G01N 29/04 | (2006.01) |
| G21F 5/12 | (2006.01) |

(52) U.S. Cl.
CPC ............ *G21F 5/008* (2013.01); *B23K 5/08* (2013.01); *B23K 9/028* (2013.01); *B23K 9/18* (2013.01); *B23K 10/02* (2013.01); *B23K 11/093* (2013.01); *B23K 23/00* (2013.01); *B23K 25/00* (2013.01); *B65D 7/04* (2013.01); *B65D 7/38* (2013.01); *G01N 29/04* (2013.01); *G21F 5/12* (2013.01); *G01N 2291/023* (2013.01); *G01N 2291/0289* (2013.01); *G21F 2005/125* (2013.01)

(58) Field of Classification Search
CPC ....... G21F 5/00; G21F 5/008; A62D 2203/10; B23K 5/08
USPC .................................................. 588/16, 900
See application file for complete search history.

(56) References Cited

U.S. PATENT DOCUMENTS

| | | |
|---|---|---|
| 4,596,688 A | 6/1986 | Popp |
| 5,161,413 A | 11/1992 | Junker et al. |
| 2004/0020919 A1 | 2/2004 | Hirano et al. |
| 2008/0265182 A1 | 10/2008 | Singh et al. |
| 2011/0049155 A1 | 3/2011 | Levine et al. |

OTHER PUBLICATIONS

Corresponding International Search Report and Written Opinion for PCT/US13/77852 dated May 21, 2014.

*Primary Examiner* — Edward Johnson
(74) *Attorney, Agent, or Firm* — The Belles Group, P.C.

(57) ABSTRACT

A canister for storing radioactive materials includes a base plate, side wall and a top plate. The top plate includes a top surface with a top edge having a bevel, and with a channel set in from the top edge. The top plate is sealed to the sidewall by a weld formed between the beveled top edge and the top of the side wall. The base plate is sealed to a bottom of the sidewall, so that a sealed vessel is formed.

10 Claims, 8 Drawing Sheets

FIG. 5B

RADIOACTIVE MATERIAL STORAGE CANISTER

CROSS REFERENCE TO RELATED APPLICATIONS

The present application is a National Stage application under 35 U.S.C. §371 of International Application No. PCT/US2013/077852 filed Dec. 26, 2013, which claims priority to U.S. provisional application No. 61/746,094 filed Dec. 26, 2012, the disclosures of which are incorporated by reference in their entireties.

FIELD OF THE INVENTION

The field of the present invention relates to radioactive materials storage canisters.

BACKGROUND OF THE INVENTION

Virtually all of the used nuclear fuel produced in the United States and a significant quantity generated overseas is stored in sealed canisters that have their parts welded together. These canisters are sometimes referred to as multi-purpose canisters (MPCs). MPCs are mostly manufactured from austenitic stainless steel but exotic alloys such as Hastaloy, Inconel, etc., have also been considered. The typical MPC includes two major parts, the first part being formed from an outer a cylindrical vessel having a shop-welded bottom (base plate) and a flat top lid which is welded to the top of the cylindrical vessel at the nuclear plant after the fuel is loaded inside the MPC. The outer body of the completed MPC is also referred to as an "enclosure vessel". The second part is the internal structure, called a fuel basket, which stores the nuclear fuel in the desired configuration. An MPC may also be used to store other forms of high level waste, although for ease of discussion the term "spent fuel" is used to represent all forms of high level waste.

The enclosure vessel is responsible for maintaining confinement of its radiological contents including gaseous matter, under all normal, off-normal, and accident design conditions. The physical integrity of the pressure retention and confinement boundary of an MPC is a fundamental safety requirement during storage and transport. Accordingly, to ensure maximum protection against leakage, the enclosure vessel is made using the rules of ASME Section III Class 1, which is the most rigorous pressure vessel code in use in the United States. Pursuant to the provisions for Class 1 components in Section III of the Code, all pressure boundary material in the Enclosure Vessel is ultrasonically examined and all body welds are subject to 100% volumetric examination (e.g., radiography or ultrasonic testing (UT)). The state of the art, however, does not enable 100% volumetric examination of the top lid of the MPC because the top lid can only be welded in the field, after the canister has been loaded with spent fuel. The process of sealing the canister is therefore necessarily performed in the presence of a high radiation field around the canister so that weld crews have limited physical access to the canister when it is sealed due to the high radiation doses to which they would be exposed. Prompted by the need to prevent large dose exposure to the crew, the lid-to-shell (LTS) weld joint has historically been made as a partial penetration half-V groove or J-groove weld (see FIG. 1). Such a weld is readily made by an automated weld machine having a weld arm designed to traverse the circular weld-path. The drawback is that the partial penetration weld cannot be 100% volumetrically examined with an acceptable level of accuracy. However, the USNRC permits the root weld and successive passes to be examined using by the less robust method of liquid penetrant (LP) examination. Because LP is a surface examination tool, the soundness of the weld mass located between successive LP examinations cannot actually be examined.

Efforts to devise a UT process to volumetrically examine the partial penetration closure weld thus far have not been successful. State-of the-art UT technology is capable of providing high quality volumetric examination of the entire closure weld mass with only a small "blind spot" located at the tip of the root pass area. There are proposals to perform liquid penetrant examination of the root pass to confirm its quality, and after the root pass has been checked for soundness, the balance of the weld mass may be examined by UT. Regardless, although the risk of a hidden flaw in the closure weld propagating under a storage or transport event is extremely small, given the use of highly fracture resistant austenitic stainless steel material in the MPCs, the lack of the ability to subject the entire weld mass to 100% volumetric examination remains a weakness for enclosure vessels.

SUMMARY OF THE INVENTION

The present invention is directed toward a canister for storing radioactive materials. The lid of the canister is configured so that the entire volume of the weld between the lid and the side wall of the canister may be subjected to a volumetric examination.

In a first separate aspect of the present invention, a canister for storing radioactive materials includes a top plate, a base plate, and a side wall sealed together to form a sealed vessel. The top plate includes a top surface with a top edge having a bevel and with a channel set in from the top edge. The top plate is sealed to the side wall by a weld formed between the beveled top edge and the top of the side wall. The base plate is sealed to the bottom of the side wall.

In a second separate aspect of the present invention, a method of forming a sealed canister includes placing a top plate on a top opening of a side wall, with the bottom of the side wall being sealed to a base plate. The top plate includes a top surface with a top edge having a bevel and with a channel set in from the top edge. A weld is formed between the beveled top edge and the top opening of the side wall to seal the top plate to the side wall, thereby forming the sealed canister.

In a third separate aspect of the present invention, a method of storing radioactive materials includes placing radioactive materials in a cavity formed by a side wall having a bottom sealed to a base plate. A top plate is placed on a top opening of the side wall, wherein the top plate includes a top surface with a top edge having a bevel and with a channel set in from the top edge. A weld is formed between the beveled top edge and the top opening of the side wall to seal the top plate to the side wall, so that the cavity is hermetically sealed. A first probe is placed in the channel, and a second probe is placed adjacent the side wall opposite the first probe, such that the weld is disposed between the two probes. The first and second probes are activated to determine an integrity of a volume of the weld between the probes, and the probes are moved synchronously around the top plate to determine the integrity of an entire volume of the weld.

In a fourth separate aspect of the present invention, any of the foregoing aspects may be employed in combination.

Accordingly, an improved canister for storing radioactive materials and a method of sealing the same are disclosed. Advantages of the improvements will be apparent from the drawings and the description of the preferred embodiment.

BRIEF DESCRIPTION OF THE DRAWINGS

The foregoing summary, as well as the following detailed description of the exemplary embodiments, will be better understood when read in conjunction with the appended drawings. It should be understood, however, that the invention is not limited to the precise arrangements and instrumentalities shown in the following figures.

DETAILED DESCRIPTION OF THE INVENTION

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the preferred embodiments. Accordingly, the invention expressly should not be limited to such preferred embodiments illustrating some possible non-limiting combinations of features that may exist alone or in other combinations of features; the scope of the invention being defined by the claims appended hereto.

Figure 1:
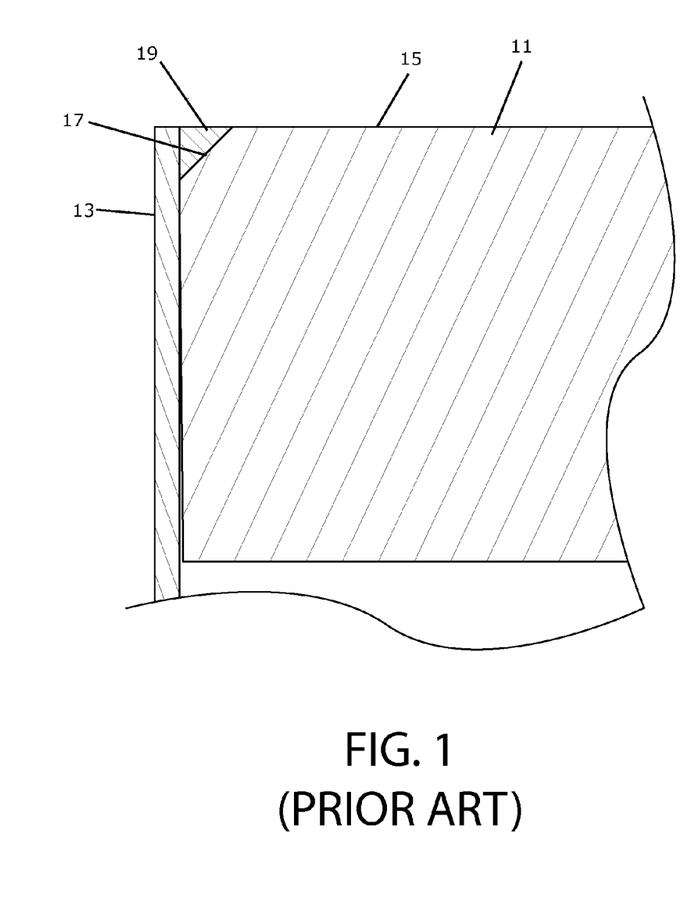
FIG. 1 illustrates the top lid welded to the side wall of a canister according to the prior art.

The lid 11 and top portion of a side wall 13 for an MPC of the prior art are shown in FIG. 1. The top surface 15 of the lid 11 includes a beveled edge 17, and the closure weld 19 joining the lid 11 to the side wall 13 is formed in the space between the half V-shaped space between the beveled edge 17 and the top portion of the side wall 13. As shown, the weld is a through-thickness single groove weld V-shaped groove, although the groove could instead be J-shaped. Due the physical configuration of the lid, the sidewall, and the closure weld, this type of closure weld is not susceptible to 100% volumetric examination.

Figure 2A:
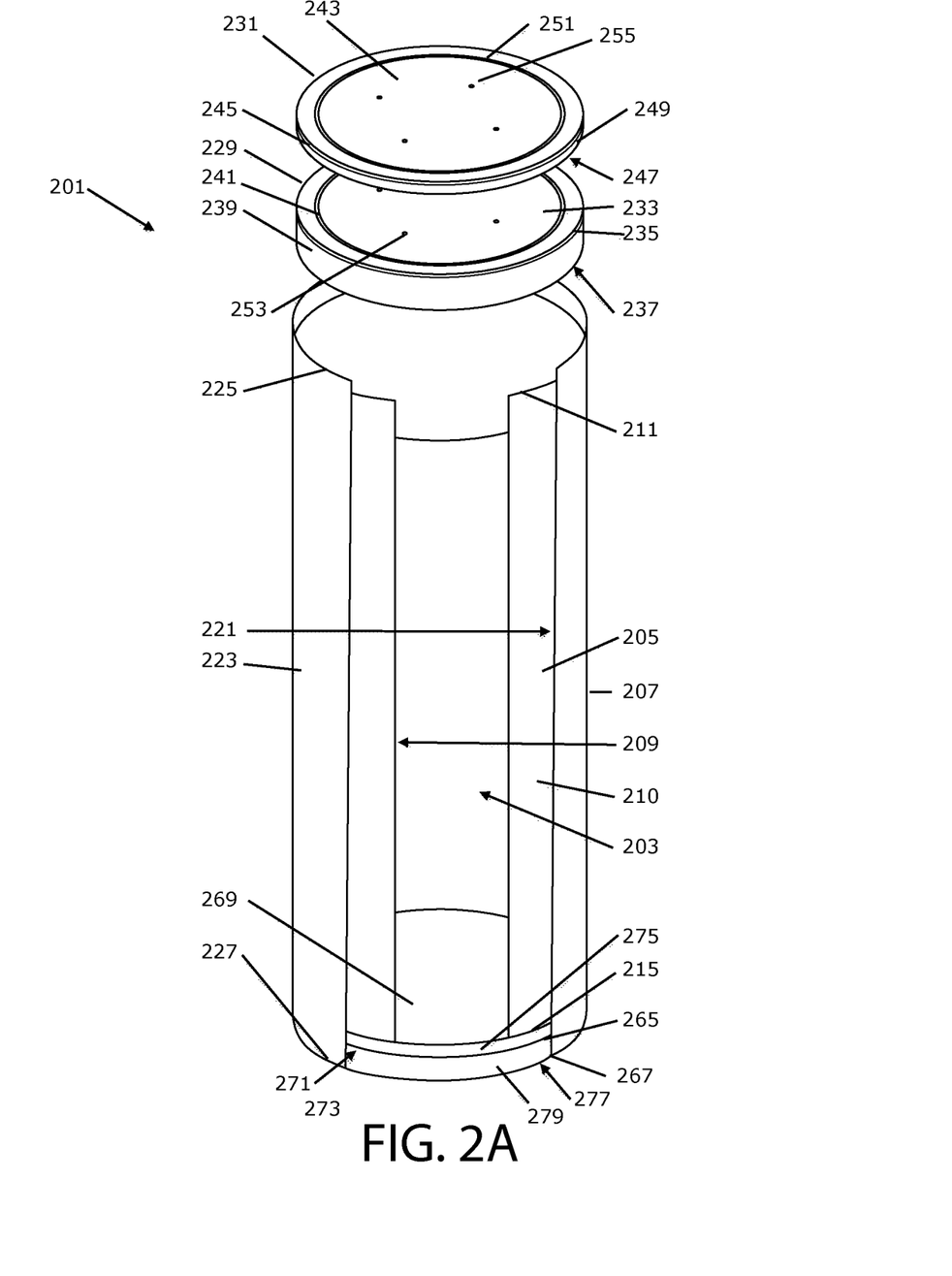
FIG. 2A illustrates a double-walled MPC having lids configured to allow 100% volumetric examination of the respective closure weld.

A dual-walled MPC 201 is illustrated in FIG. 2A, and this MPC 201 is configured so that the closure weld may be subjected to 100% volumetric examination. The dual-walled MPC 201 may be used with any style of fuel basket, such as the one described in U.S. Pat. No. 5,898,747, issued Apr. 27, 1999. In some instances it may be possible to use the dual-walled MPC 201 without a fuel basket, depending on the intended function. Furthermore, the dual-walled MPC 201 may be used to store and/or transport any type of high level radioactive materials and is not limited to spent nuclear fuel.

As will become apparent from the structural description below, the dual-walled MPC 201 creates two independent containment boundaries about the storage cavity 203 which operate to contain both fluidic (gas and liquid) and particulate radiological matter within the cavity 203. As a result, if one containment boundary were to fail, the other containment boundary will remain intact. While theoretically the same, the containment boundaries formed by the dual-walled MPC 201 about the cavity 203 can be literalized in many ways, including without limitation a gas-tight containment boundary, a pressure vessel, a hermetic containment boundary, a radiological containment boundary, and a containment boundary for fluidic and particulate matter. These terms are used synonymously throughout this application. In one instance, these terms generally refer to a type of boundary that surrounds a space and prohibits all fluidic and particulate matter from escaping from and/or entering into the space when subjected to the required operating conditions, such as pressures, temperatures, etc.

Finally, while the dual-walled MPC 201 is illustrated and described in a vertical orientation, it is to be understood that the dual-walled MPC 201 can be used to store and/or transport its load in any desired orientation, including at an angle or horizontally. Thus, use of all relative terms through this specification, including without limitation "top," "bottom," "inner" and "outer," are used for convenience only and are not intended to be limiting of the invention in such a manner.

The dual-walled MPC 201 includes a first shell that acts as an inner shell 205 and a second shell that acts as an outer shell 207. The inner and outer shells 205, 207 are preferably cylindrical tubes and are constructed of a metal. Of course, other shapes can be used if desired. The inner shell 205 is a tubular hollow shell that includes an inner surface 209, an outer surface 210, a top edge 212 and as bottom edge 215. The inner surface 209 of the inner shell 205 forms a cavity/space 203 for receiving and storing SNF. The cavity 203 is a cylindrical cavity formed about as central axis.

The outer shell 207 is also a tubular hollow shell that includes an inner surface 221, an outer surface 223, a top edge 225 and a bottom edge 227. The outer shell 207 circumferentially surrounds the inner shell 205. The inner shell 205 and the outer shell 207 are constructed so that the inner surface 221 of the outer shell 207 is in substantially continuous surface contact with the outer surface 223 of the inner shell 205. In other words, the interface between the inner shell 205 and the outer shell 207 is substantially free of gaps/voids such that the two shells 205, 207 are in conformal contact. This can be achieved through an explosive joining, a cladding process, a roller bonding process and/or a mechanical compression process that bonds the inner shell 205 to the outer shell 207. The continuous surface contact at the interface between the inner shell 205 and the outer shell 207 reduces the resistance to the transmission of heat through the inner and outer shells 205, 207 to a negligible value. Thus, heat emanating from the spent nuclear fuel loaded within the cavity 203 can efficiently and effectively be conducted outward through the shells 205, 207 where it is removed from the outer surface 223 of the outer shell via convection.

The inner and outer shells 205, 207 are preferably both made of a metal. As used herein, the term metal refers to both pure metals and metal alloys. Suitable metals include without limitation austenitic stainless steel and other alloys including Hastelloy™ and Inconel™. Of course, other materials can be utilized. The thickness of each of the inner and outer shells 205, 207 is preferably in the range of 5 mm to 25 mm. The outer diameter of the outer shell 207 is preferably in the range of 1700 mm to 2000 mm. The inner diameter of the inner shell 205 is preferably in the range of 1700 mm to 1900 mm. The specific size and/or thickness of the shells 205, 207, however, is a matter of design choice.

In some embodiments, it may be further preferable that the inner shell 205 be constructed of a metal that has a coefficient of thermal expansion that is equal to or greater than the coefficient of thermal expansion of the metal of which the outer shell 207 is constructed. Thus, when the spent nuclear fuel that is stored in the cavity 203 emits heat, the outer shell 207 will not expand away from the inner shell 205. This ensures that the continuous surface contact between the outer surface 210 of the inner shell 205 and the outer surface 223 of the outer shell 207 will be maintained and a gaps will not form under heat loading conditions.

The dual-walled MPC 201 also includes a first top plate that acts as an inner top lid 229 for the inner shell 205 and a second top plate that acts as an outer top lid 231 for the outer shell 207. The inner and outer top lids 229, 231 are plate-like structures that are preferably constructed of the same materials discussed above with respect to the shells 205, 207. Preferably the thickness of the inner top lid 229 is in the range of 99 mm to 300 mm. The thickness of the outer top lid 231 is preferably in the range of 50 mm to 150 mm. The invention is not, however, limited to any specific dimensions, which will be dictated on a case-by-case basis and the radioactive levels of the spent nuclear fuel to be stored in the cavity 203.

The inner top lid 229 includes a top surface 233 with a beveled edge 235, a bottom surface 237, an outer lateral surface/edge 239, and a channel 241 formed in the top surface 233 and set in from the beveled edge 235. The outer top lid 231 includes a top surface 243 with a beveled edge 245, a bottom surface 247, an outer lateral surface/edge 249, and a channel 251 formed in the top surface 243 and set in from the beveled edge 245. When fully assembled, the outer lid 231 is positioned atop the inner lid 229 so that the bottom surface 247 of the outer lid 231 is in substantially continuous surface contact with the top surface 233 of the inner lid 229. Both the inner top lid 229 and the outer top lid 231 also include vent and/or drain ports 253, 255.

During loading procedure involving spent nuclear fuel, the cavity 203 is loaded with the spent nuclear fuel, then the inner top lid 229 is positioned so as to enclose the top end of the cavity 203 and rests atop brackets (not shown). Once the inner top lid 229 is in place, a closure weld is formed to seal the inner top lid 229 to the inner shell 205. The top lid 229 may be welded to the inner shell 205 using any suitable welding technique or combinations of techniques that use a filler material. Examples of suitable welding techniques include resistance seam welding, manual metal arc welding, metal inert gas welding, tungsten inert gas welding, submerged arc welding, plasma arc welding, gas welding, electroslag welding, thermit welding.

After the cavity 203 is sealed by the closure weld, it may then be evacuated/dried via the appropriate method and backfilled with nitrogen, helium or another inert gas using the ports 249 of the inner lid 229 that form passageways into the cavity 203. The ports 249 may thereafter be filled with a metal or other wise plugged so as to hermetically seal the cavity 203.

The outer shell 207 has an axial length that is greater than the axial length of the inner shell 205. As such, the top edge 225 of the outer shell 207 extends beyond the top edge 211 of the inner shell 205. Similarly, the bottom edge 227 of the outer shell 207 extends beyond the bottom edge 215 of the inner shell 205.

The offset between the top edges 211, 225 of the shells 205, 207 allows the top edge 211 of the inner shell 205 to act as a ledge for receiving and supporting the outer top lid 231. When the inner top lid 229 is in place, the inner surface 209 of the inner shell 205 extends over the outer lateral edges 239. When the outer top lid 231 is then positioned atop the inner lid 229, the inner surface 221 of the outer shell 207 extends over the outer lateral edge 249 of the outer top lid 231. The top edge 225 of the outer shell 207 is substantially flush with the top surface 253 of the outer top lid 231. The inner and outer top lids 229, 231 are welded to the inner and outer shells 205, 207 respectively after the fuel is loaded into the cavity 203. Similar to the inner top lid 229, once the outer top lid 231 is in place, a closure weld is formed to seal the outer top lid 231 to the outer shell 207. The outer top lid 231 may be welded to the outer shell 207 using any suitable welding technique or combinations of techniques that use a filler material. Examples of suitable welding techniques include resistance seam welding, manual metal arc welding, metal inert gas welding, tungsten inert gas welding, submerged arc welding, plasma arc welding, gas welding, electroslag welding, thermit welding. The closure welds sealing the inner and outer top lids 229, 231 to the inner and outer shells 205, 207 may be subjected to 100% volumetric examination once the welds are formed. It is to be understood that the closure weld for the inner top lid 229 is to undergo volumetric examination before the outer top lid 231 put in place.

The dual-walled MPC 201 also includes a first plate that acts as an inner base plate 265 and a second plate that acts as an outer base plate 267. The inner and outer base plates 265, 267 are rigid plate-like structures having circular horizontal cross-sections. The invention is not so limited, however, and the shape and size of the base plates is dependent upon the shape of the inner and outer shells. The inner base plate 265 includes a top surface 269, a bottom surface 271 and an outer lateral surface/edge 273. Similarly, the outer base plate 267 includes a top surface 275, a bottom surface 277 and an outer lateral surface/edge 279.

The top surface 269 of the inner base plate 265 forms the floor of the cavity 203. The inner base plate 265 rests atop the outer base plate 267. Similar to the other corresponding components of the dual-walled MPC 201, the bottom surface 271 of the inner base plate 265 is in substantially continuous surface contact with the top surface 275 of the outer base plate 267. As a result, the interface between the inner base plate 265 and the outer base plate 267 is free of gaseous gaps/voids for thermal conduction optimization. An explosive joining, a cladding process, a roller bonding process and/or a mechanical compression process can be used to effectuate the contact between the base plates 265, 267. Preferably, the thickness of the inner base plate 265 is in the range of 50 mm to 150 mm. The thickness of the outer base plate 267 is preferably in the range of 99 mm to 200 mm. Preferably, the length from the top surface of the outer top lid 231 to the bottom surface of the outer base plate 267 is in the range of 4000 mm to 5000 mm, but the invention is in no way limited to any specific dimensions.

The outer base plate 267 may be equipped on its bottom surface with a grapple ring (not shown) for handling purposes. The thickness of the grapple ring is preferably between 50 mm and 150 mm. The outer diameter of the grapple ring is preferably between 350 mm and 450 mm.

The inner shell 205 rests atop the inner base plate 265 in a substantially upright orientation. The bottom edge 215 of the inner shell 205 is connected to the top surface 275 of the inner base plate 265 by a through-thickness single groove (V or J shape) weld. The outer surface 210 of the inner shell 205 is substantially flush with the outer lateral edge 273 of the inner base plate 265. The outer shell 207, which circumferentially surrounds the inner shell 205, extends over the outer lateral edges 273, 279 of the inner and outer base plates 265, 267 so that the bottom edge 227 of the outer shell 207 is substantially flush with the bottom surface 277 of the outer base plate 267. The inner surface 221 of the outer shell 207 is also connected to the outer base plate 267 using a through-thickness edge weld. In an alternative embodiment, the bottom edge 227 of the outer shell 207 could rest atop the top surface 275 of the outer base plate 267 (rather than extending over the outer later edge of the base plate 267). In such an embodiment, the bottom edge 227 of the outer shell 207 could be welded to the top surface 275 of the outer base plate 267.

When all of the seal and closure welds discussed above are completed, the combination of the inner shell 205, the inner base plate 265 and the inner top lid 229 forms a first hermetically sealed structure surrounding the cavity 203, thereby creating a first pressure vessel. Similarly, the combination of the outer shell 207, the outer base plate 267, and the outer top lid 231 form a second sealed structure about the first hermetically sealed structure, thereby creating a second pressure vessel about the first pressure vessel and the cavity 203. Theoretically, the first pressure vessel is located within the internal cavity of the second pressure vessel. Each pressure vessel is engineered to autonomously meet the stress limits of the ASME Code with significant margins.

Figure 2B:
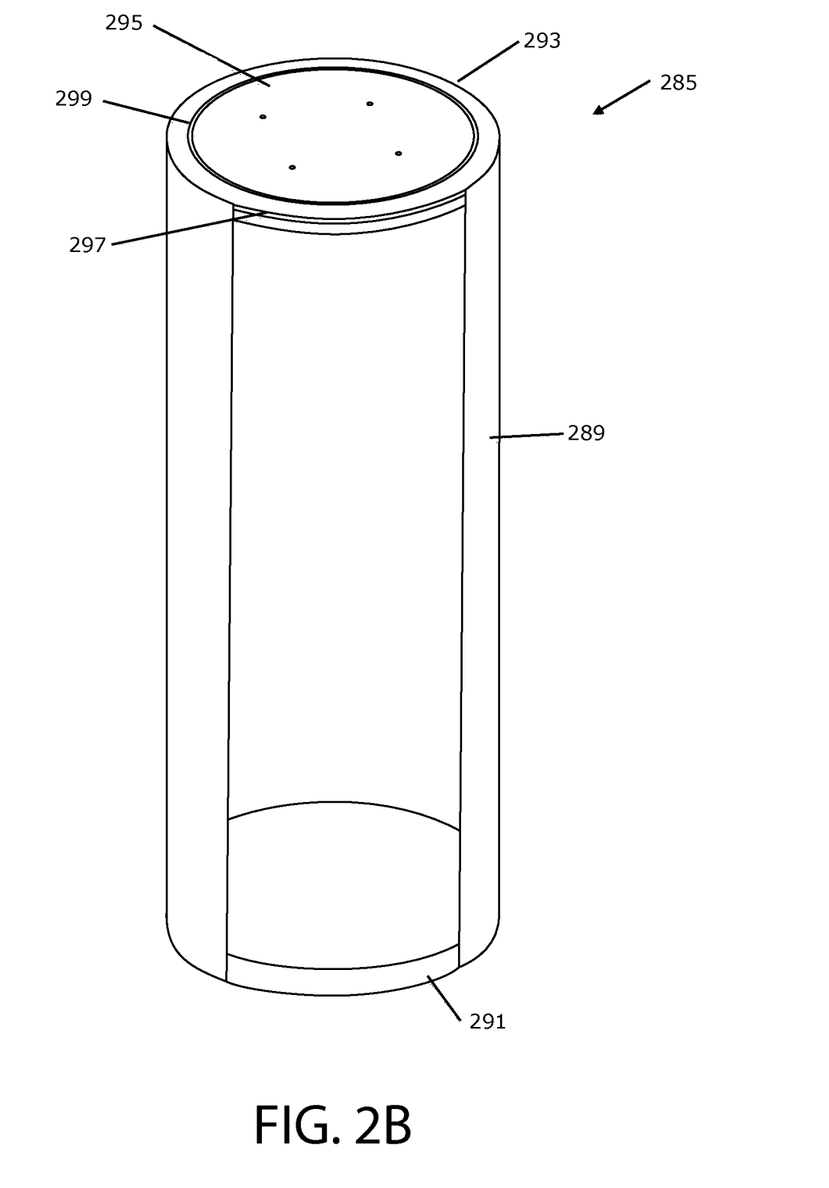
FIG. 2B illustrates a single walled MPC having a lid configured to allow 100% volumetric examination of the closure weld.

FIG. 2B illustrates a single-walled MPC 285 which is constructed in a similar manner as each pressure vessel of the double-walled MPC 201 discussed above. This single-walled MPC 287 includes a side wall 289 seal welded to a base plate 291, and a top plate 293. The top surface 295 of the top plate 293 includes a beveled top edge 297 and a channel 299 set in from the top edge 297. Having the lid configured with the channel 299 makes it so that the closure weld may be subjected to 100% volumetric examination. All other parts of the single-walled MPC 285 may be constructed in the same manner described above.

Figure 2C:
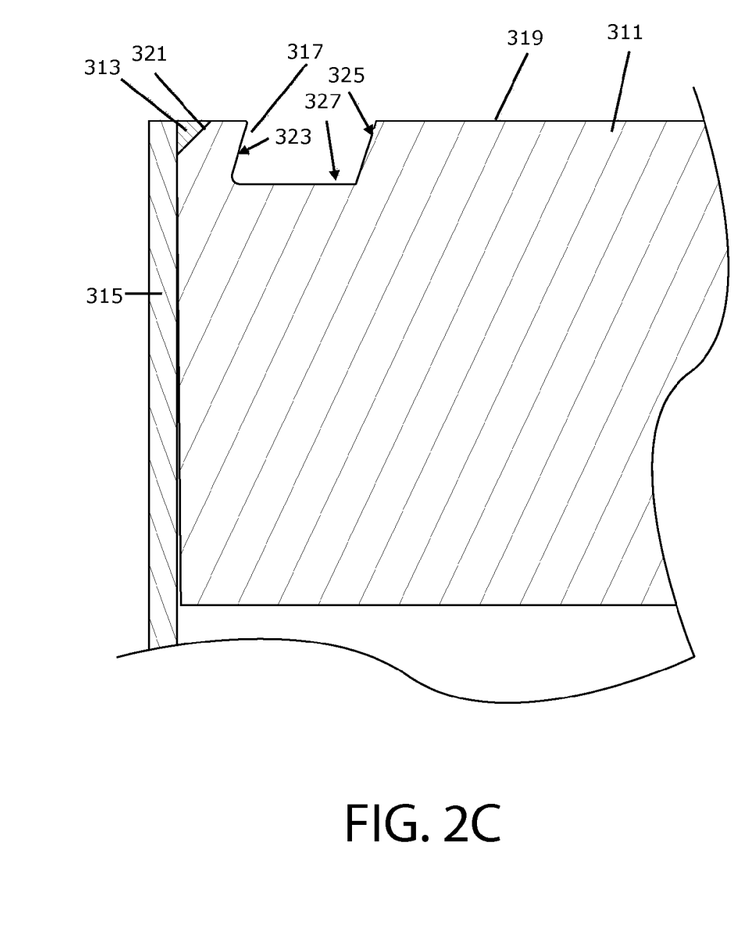
FIG. 2C illustrates a detailed sectional view of a lid and closure weld, the lid being configured to allow 100% volumetric examination of the closure weld.

A detailed view a top plate 311 and the closure weld 313 sealing the top plate 311 to a side wall 315 of an MPC are illustrated in FIG. 2C. The channel 317 in the top surface 319 is set in from the beveled top edge 321. The channel 317 extends below the top surface 319 at least as much as does the bevel of the beveled top edge 321. In some embodiments, depending upon the configuration of the probe being used, it may be desirable to have the channel 317 extend deeper below the top surface than the bevel in order to accommodate the probe. The channel 317 is sufficiently wide so that a probe used for examining the closure weld may be placed within the channel 317 and moved circumferentially around the top plate 311 for purposes of achieving 100% volumetric examination of the closure weld. For some types of probes, the channel may be as wide as 2" to 3", although these dimensions may vary significantly to accommodate the configuration of the probe used to examine the closure weld. The side wall 323 of the channel 317 nearest the beveled top edge 321 is placed at an angle that is approximately parallel to the angle of the beveled top edge 321. However, in some embodiments the angle of this channel side wall may vary from the angle of the top beveled edge by 5°-20° or more, depending upon the configuration of probe being used. The side wall 323, however, may be formed at any angle relative to the beveled top edge 321. The opposite wall 325 of the channel 317 may have any configuration, from a well-defined wall, as is shown, to a curved or flat surface adjoining the bottom 327 of the channel 317.

Figure 3:
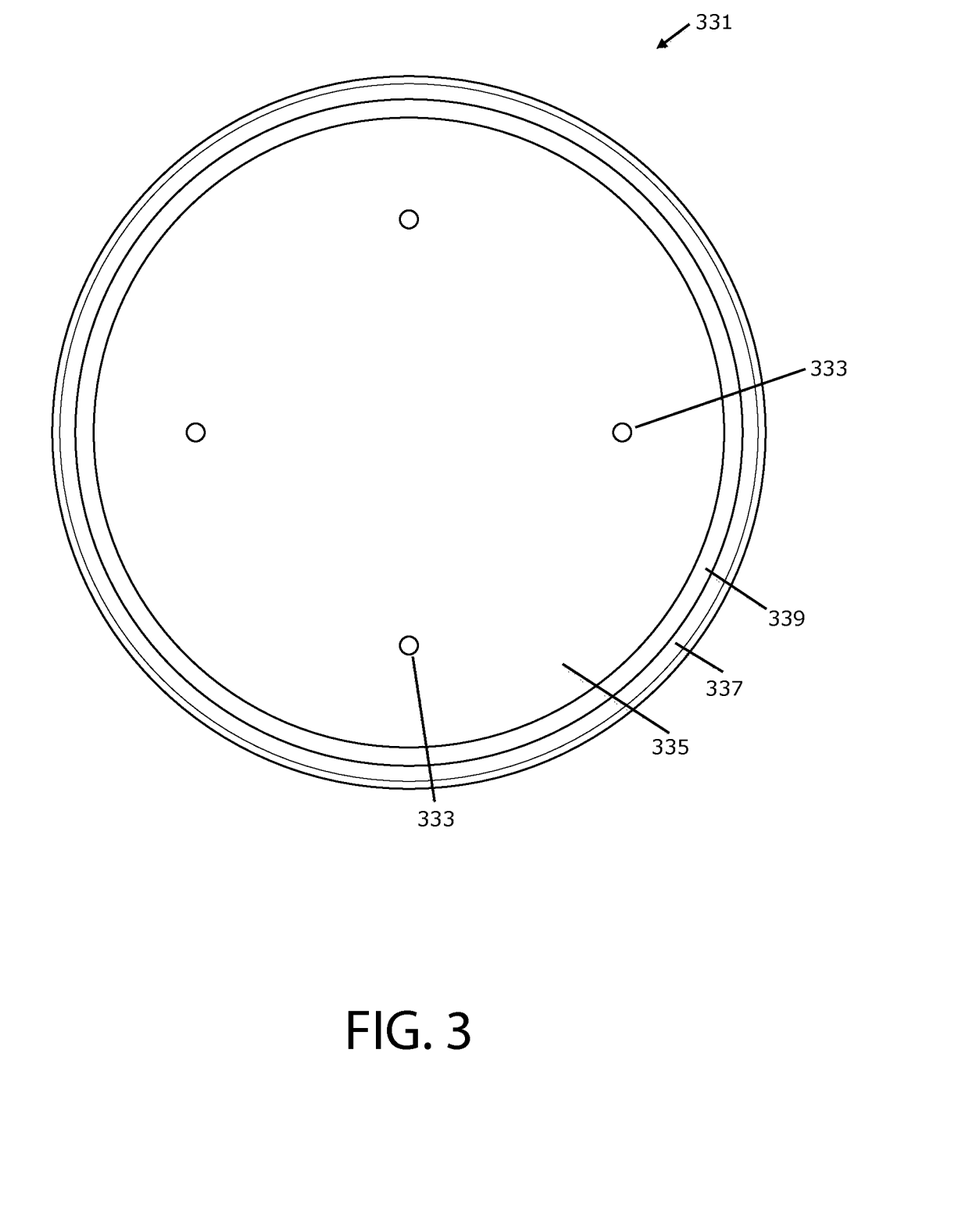
FIG. 3 illustrates a top elevation view of a first lid configured to allow 100% volumetric examination of the closure weld.
Figure 4:
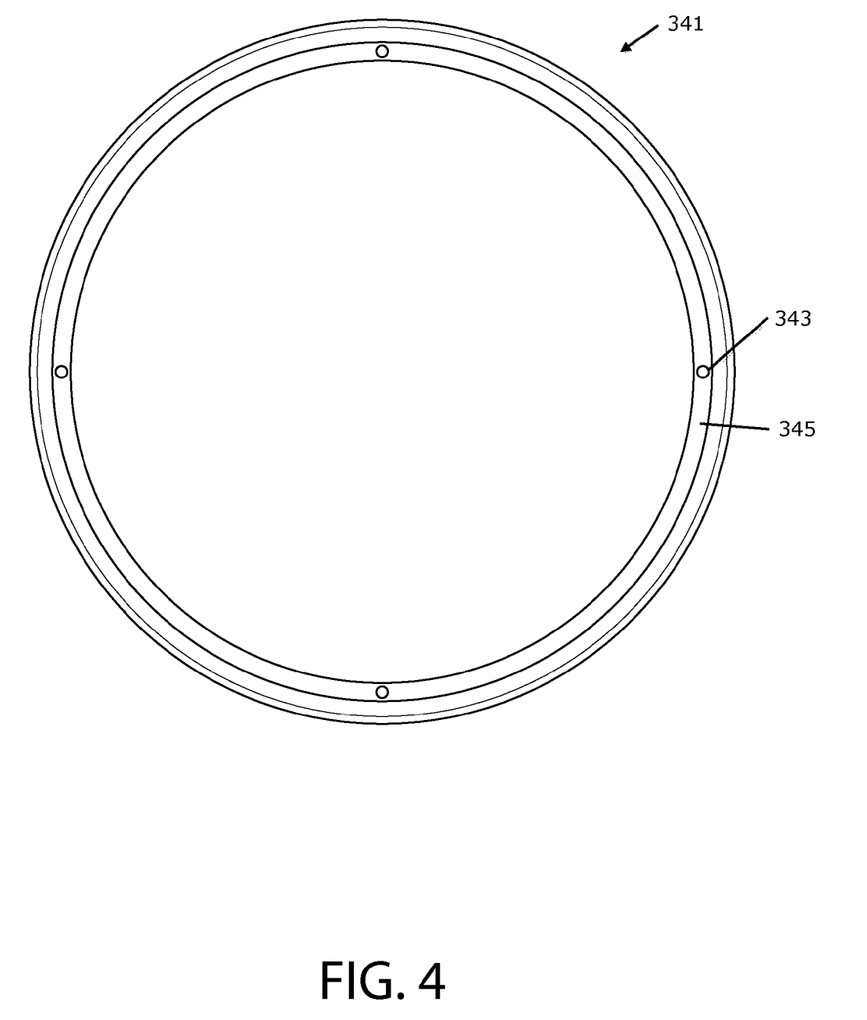
FIG. 4 illustrates a top elevation view of a second lid configured to allow 100% volumetric examination of the closure weld.

One embodiment of a top plate 331 is shown in FIG. 3 with ports 333 positioned in the central portion 335 of the top surface 337 of the top plate 331, radially inward from the channel 339. The ports 333 may serve any desired purpose for the MPC for which the top plate 331 is used, and the different ports may be used for different purposes. Examples of purposes for the ports include their use as vent ports, as vacuum ports, as drain ports, as backfill ports, as test ports, among others. Another embodiment of a top plate 341 is shown in FIG. 4. In this embodiment, the ports 343 are positioned within the channel 345. In other embodiments, ports may be positioned both within the channel and in the central portion of the top surface of the top plate.

Figure 5A:
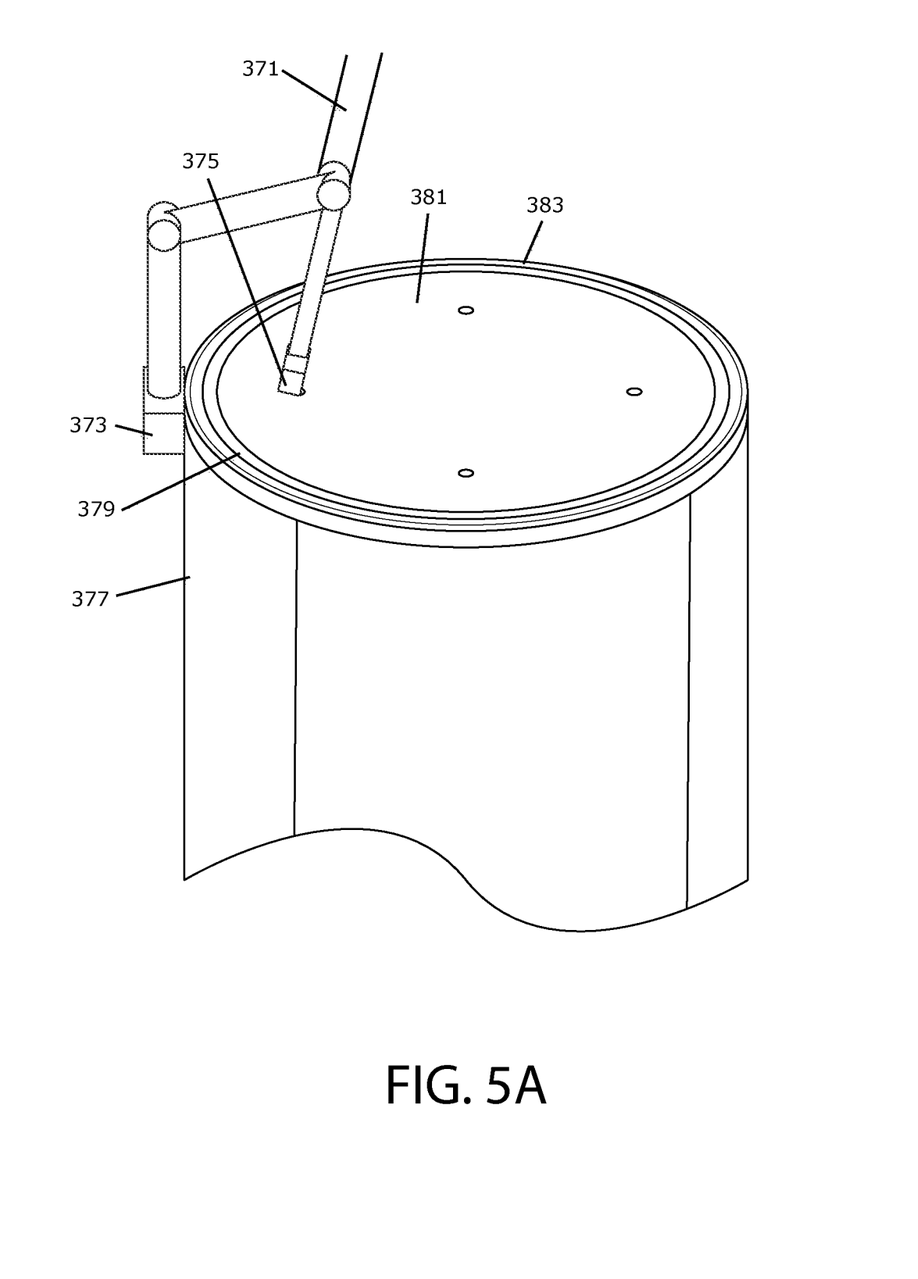
FIG. 5A illustrates a weld arm positioned to form a closure weld and probes positioned to volumetrically examine the closure weld.
Figure 5B:
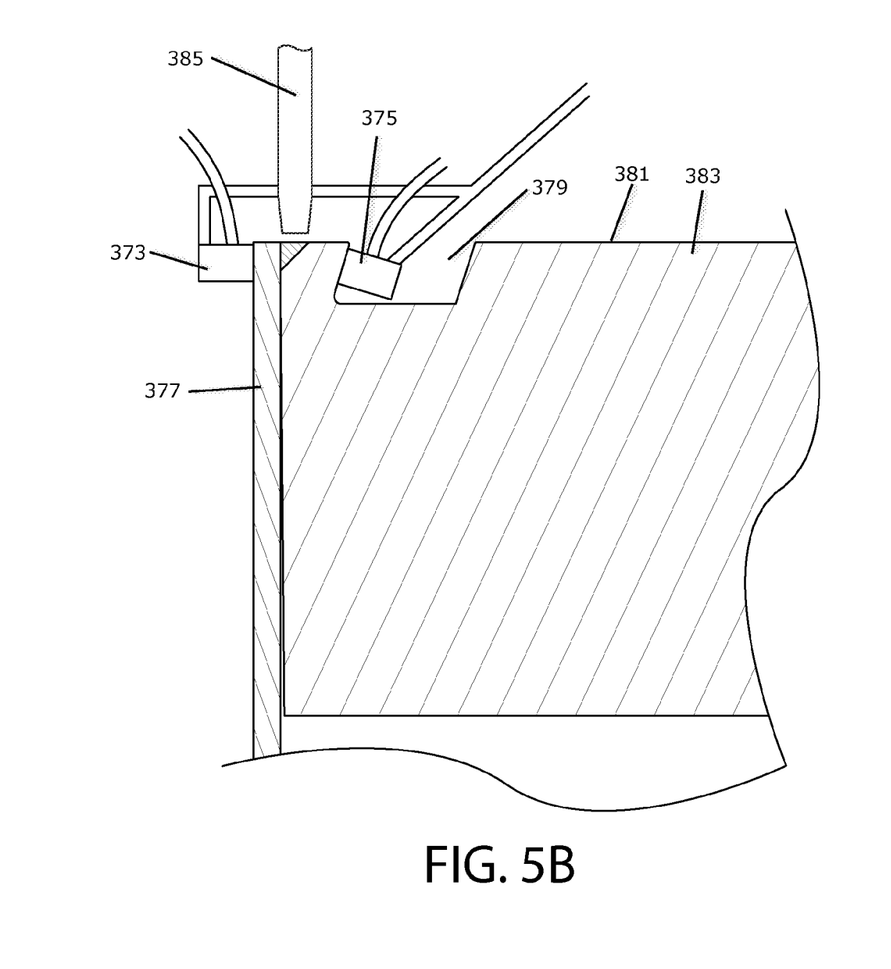
FIG. 5B illustrates a detailed sectional view of a lid, the weld head, and the probes of FIG. 5A.

FIGS. 5A and 5B illustrate the process of performing the 100% volumetric examination of the closure weld after it has been formed. With the top plate in place on the top opening of the sidewall, the top plate having a channel as described above, the closure weld may be formed by automated equipment, such as is well known in the art. In order to volumetrically examine the closure weld, probes are mounted on a support arm capable of rotating and positioning the probes to perform the volumetric examination of the closure weld. For example, the probes may be mounted on the same type of weld arm that is used in the automated process for forming the closure weld. The volumetric examination may be carried out once the entire weld is formed.

Only the end of the support arm 371 is illustrated in FIG. 5A to simplify the drawing. It is to be understood that the support arm may have any appropriate configuration that is capable of supporting the probes and moving them around the top plate to perform the volumetric examination, as many different types and configurations of such support arms are well-known in the arts, including combination rotary/articulating robotic arms. Two probes 373, 375 are affixed to the end of the support arm 371, and the support arm is configured for automated or remote positioning of the probes so that the volumetric examination of the closure weld may be performed. The first probe 373 is positioned on the outside of the top of the side wall 377, and the second probe 375 is shown just prior to being positioned within the channel 379 funned in the top surface 381 of the top plate 383. This second probe 375 is shown positioned within the channel 379 in FIG. 5B. Once the two probes are in position, the entire volume of a portion of the closure weld is disposed between the two probes, and that entire volume may be volumetrically examined. By activating the two probes and moving them synchronously around the top plate, maintaining their relative position with respect to the closure weld, the entirety of the weld is passed between the two probes in one circumscription of the top plate. It is therefore possible, with the appropriate examination technology, to perform a 100% volumetric examination of the closure weld. Using well-known processes associated with the selected examination technology, the integrity of the entire closure weld may be determined from the examination.

In the embodiment of FIG. 5A, the entire closure weld is formed first, followed by the volumetric examination of the closure weld. In the embodiment of FIG. 5B, the weld head 385 extends from the same support arm (not shown in FIG. 5B) as the probes 373, 375. The weld arm then moves the weld head around the top edge of the top plate to form the closure weld, and the probes trail the weld head to perform the volumetric examination. This embodiment may be used to form the weld and substantially concurrently volumetrically examine the weld. For a multi-pass closure weld, having the probes trail the weld head in this manner enables a separate volumetric examination of each pass of the closure weld. Due to the heat generated from the welding process, which may interfere with the examination process, this embodiment may be best suited for use in pools or in the presence of a coolant, such as a flow of demineralized water In certain embodiments, a Linear Scan-Phased Array UT system may be used to examine the closure weld, and for such embodiments the probes are ultrasound transducer probes. Such a UT system is capable of conducting the 100% volumetric examination of the closure weld within a matter of minutes. Beneficially, with the top plate configured as described above and with use of the two probes, no human activity needs to be directly involved for placing the top plate, forming the closure weld, or examining the integrity of the closure weld, so that work crews are not exposed to any significant doses of radiation.

In embodiments where a UT system is used outside of a pool of water or other fluid, a coupling agent, such as demineralized water or an appropriate gel, may be introduced between the transducer probes and the top plate and/or side wall to increase the amount of ultrasound energy that passes into the closure weld, thereby improving the volumetric examination. As is well known in the art of UT, only small amounts of the coupling agent are needed to form a thin film, minimizing air gaps, between the transducer probe and the parts of the MPC into which the ultrasound energy is being directed. Therefore, a simple drip system suffices to introduce a coupling agent such as de-mineralized water to the process of volumetric examination described herein.

In embodiments involving a high heat load canister, to ensure that the metal temperature of the weld mass is not too high for an accurate UT reading, it may be necessary to circulate cooling water through the MPC using the vent and drain ports in the lid before performing the volumetric examination. As an alternative, the use of a coupling agent for ultrasound energy, such as demineralized water, between the transducer probes and the MPC helps to insure that the volumetric examination is performed at a uniform temperature, thereby preserving the UT calibration integrity.

While the invention has been described with respect to specific examples including presently preferred modes of carrying out the invention, those skilled in the art will appreciate that there are numerous variations and permutations of the above described systems and techniques. It is to be understood that the concepts and ideas disclosed herein can be applied to other areas of high level radioactive waste storage, transportation and support. It is also to be understood that other embodiments may be utilized and structural and functional modifications may be made without departing from the scope of the present invention. Thus, the spirit and scope of the invention should be construed broadly as set forth in the appended claims.

What is claimed is:

1. A canister for storing radioactive materials, the canister comprising:
   a base plate;
   a side wall having a bottom sealed to the base plate; and
   a top plate including a top surface with a top edge having a bevel and with an annular channel set in from the top edge, wherein a weld is formed between the beveled top edge and a top of the side wall to seal the top plate to the side wall, and
   wherein the base plate, side wall, and top plate form a sealed vessel.

2. The canister of claim 1, wherein the base plate, side wall, and top plate form a hermetically sealed vessel.

3. The canister of claim 1, wherein the circumferential channel is approximately as deep as the bevel extends below the top surface.

4. The canister of claim 1, wherein the circumferential channel is deeper than the bevel extends below the top surface.

5. The canister of claim 1, wherein the top plate includes one or more ports therethrough.

6. The canister of claim 1, wherein at least one of the ports is disposed in the channel.

7. The canister of claim 1, wherein the side wall forms one of two walls of a double-walled canister.

8. The canister of claim 1, wherein the top plate is monolitihic.

9. The canister of claim 1, wherein the annular channel circumscribes a raised central portion and the annular channel is circumscribed by a perimeter portion.

10. The canister of claim 9, wherein the raised central portion and the perimeter portion each have a top surface that are substantially coplanar.

\* \* \* \* \*